United States Patent
Schneider et al.

(10) Patent No.: US 9,952,145 B2
(45) Date of Patent: Apr. 24, 2018

(54) RADIATION DETECTOR FOR A NON-DISPERSIVE INFRARED GAS ANALYZER

(71) Applicant: Emerson Process Management GmbH & Co. OHG, Wessling (DE)

(72) Inventors: Rudolf Schneider, Bad Orb (DE); Leif Knoepke, Hanau (DE); Marc Winter, Erlensee (DE); Erich Wombacher, Bessenbach (DE)

(73) Assignee: Emerson Process Management GmbH & Co. OHG, Wessling (DE)

( * ) Notice: Subject to any disclaimer, the term of this patent is extended or adjusted under 35 U.S.C. 154(b) by 0 days.

(21) Appl. No.: 15/569,496

(22) PCT Filed: May 3, 2016

(86) PCT No.: PCT/EP2016/059875
§ 371 (c)(1),
(2) Date: Oct. 26, 2017

(87) PCT Pub. No.: WO2016/177720
PCT Pub. Date: Nov. 10, 2016

(65) Prior Publication Data
US 2018/0088039 A1 Mar. 29, 2018

(30) Foreign Application Priority Data
May 4, 2015 (DE) .................. 10 2015 106 915

(51) Int. Cl.
*G01N 21/3504* (2014.01)
*G01N 21/61* (2006.01)

(52) U.S. Cl.
CPC .............. *G01N 21/3504* (2013.01)

(58) Field of Classification Search
CPC .... G01N 21/37; G01N 21/61; G01N 21/3504; G01N 21/317; G01N 21/3513
See application file for complete search history.

(56) References Cited

U.S. PATENT DOCUMENTS

| | | | |
|---|---|---|---|
| 5,055,688 A | 10/1991 | Fabinski | |
| 2003/0030273 A1 | 2/2003 | Shimizu et al. | |
| 2012/0120397 A1* | 5/2012 | Furtaw | G01N 21/3504 356/437 |

FOREIGN PATENT DOCUMENTS

| | | |
|---|---|---|
| DE | 25 05 006 A1 | 12/1977 |
| DE | 39 37 141 A1 | 5/1991 |

(Continued)

OTHER PUBLICATIONS

International Search Report of PCT/EP2016/059875, dated Sep. 15, 2016.

*Primary Examiner* — David Porta
*Assistant Examiner* — Faye Boosalis
(74) *Attorney, Agent, or Firm* — Collard & Roe, P.C.

(57) ABSTRACT

A radiation detector for a non-dispersive infrared gas analyzer has two detector chambers, which are surrounded by a housing and separated by a separating element permeable to infrared radiation and impermeable to gas and which can be filled with a radiation-absorbing measurement gas. A receiving element, which has a measuring system fastened therein and including a flow- or pressure-sensitive sensor, can be attached to a contact surface on an outer face of the housing. Each detector chamber is pneumatically connected to the measuring system by a channel, which extends in the housing and is open to gas. The housing of the radiation detector is modularly constructed and includes a base element, which encloses the channel, the separating element, and the measuring system fastened in the receiving element, and a first and a second outer element, each of which can be (Continued)

Figure 1:
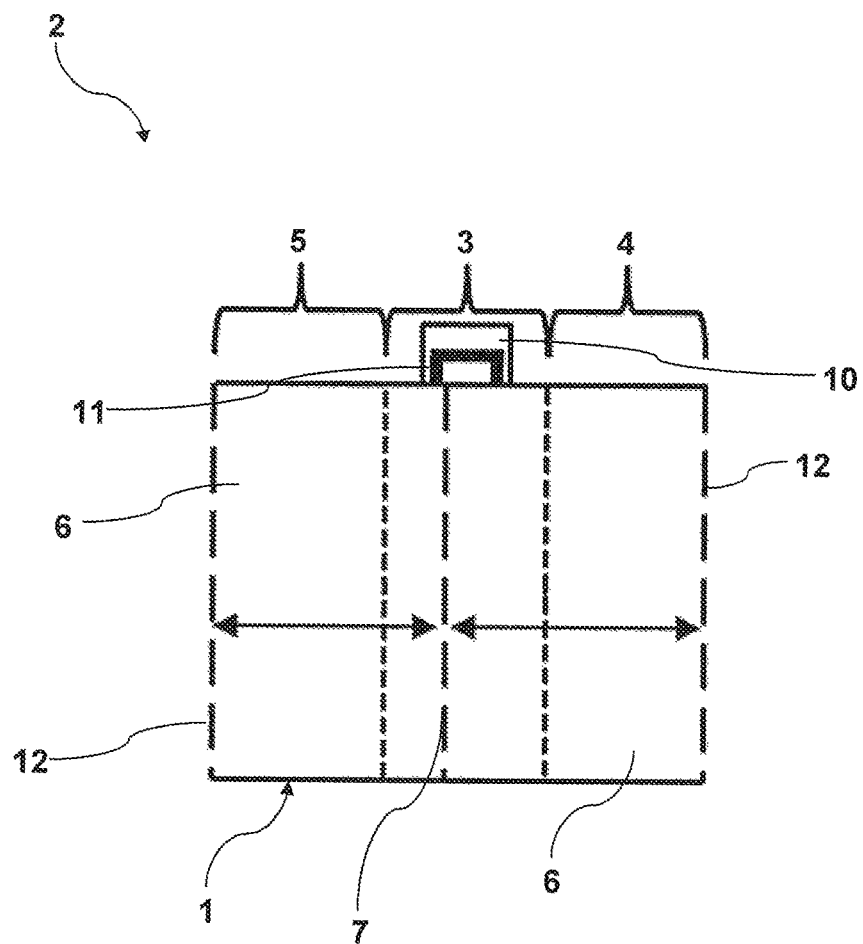

connected to the base element and surrounds a detector chamber. The outer elements have openings, which lie in the beam path of the infrared radiation and are sealed in a gas-tight manner by a radiation-permeable window. The receiving element and the first and the second outer elements are joined to the base element.

12 Claims, 4 Drawing Sheets

(56) References Cited

FOREIGN PATENT DOCUMENTS

| DE | 195 40 072 B4 | 12/2004 |
|----|---------------|---------|
| DE | 10 2006 014 007 B3 | 11/2007 |
| FR | 1 429 813 A | 2/1966 |
| GB | 1 316 082 A | 5/1973 |
| JP | 2000-356592 A | 12/2000 |
| JP | 2003-056592 A | 2/2003 |
| JP | 2003-065954 A | 3/2003 |
| JP | 2003-139701 A | 5/2003 |

* cited by examiner

RADIATION DETECTOR FOR A NON-DISPERSIVE INFRARED GAS ANALYZER

CROSS REFERENCE TO RELATED APPLICATIONS

This application is the National Stage of PCT/EP2016/059875 filed on May 3, 2016, which claims priority under 35 U.S.C. § 119 of German Application No. 10 2015 106 915.6 filed on May 4, 2015, the disclosure of which is incorporated by reference. The international application under PCT article 21(2) was not published in English.

The invention relates to a radiation detector for a non-dispersive infrared gas analyser, comprising two detector chambers which are surrounded by a housing and separated by a separating element that is permeable to infrared radiation and impermeable to gas, which detector chambers can be filled with a radiation-absorbing measuring gas, comprising a receiving element which can be attached to a contact surface on an outer face of the housing, and comprising a measuring system which is fastened in said receiving element and comprises a flow-sensitive or pressure-sensitive sensor, each detector chamber being pneumatically connected to the measuring system by means of a channel that extends in the housing and is open to gas.

Radiation detectors of the specified type are known from DE 195 40 072 B4 and form part of a non-dispersive infrared, gas analyser. Infrared radiation modulated by means of a radiation chopper device either strikes a cuvette filled with a measuring gas or a cuvette filled with an inert gas and arranged in parallel with said first cuvette. The detector is connected downstream of the cuvette and is filled with a gaseous component to be determined. The detector consists of at least one detector chamber which is connected to a pressure-sensitive or flow-sensitive sensor.

In order to be able to measure particular corrosive gases, detectors made of aluminium are used, the aluminium forming a highly resistant aluminium oxide layer subsequent to processing, which layer is produced by means of plasma polymerisation, for example. A detector of this kind is known from DE 10 2006 014 007 B3.

A non-dispersive infrared gas analyser is known from DE 39 37 141 A1 in which a cuvette filled with a reference gas is arranged next to a cuvette through which a measuring gas flows. Light beams of an infrared radiator which have been modulated by an aperture wheel pass through the relevant cuvette and a first radiation receiver arranged in the beam path of the infrared radiator. The radiation receiver comprises two chambers which are filled with a first measuring gas to be determined. The chambers are interconnected by means of a gas-carrying line, in which a pressure-sensitive sensor, for example a membrane condenser, is integrated. The quantities of gas contained in the chambers are heated differently on account of the wavelength-specific absorption of the radiation passing therethrough, such that a pressure difference is produced which can be measured by the sensor as a measure of the present gas concentration. A second radiation receiver can be connected downstream of the first radiation receiver, in which second radiation receiver a second measuring gas sample to be analysed is present. The beams strike the second radiation receiver through transparent windows integrated in the first radiation receiver, in which second radiation receiver the concentration of the second measuring gas sample can in turn be determined. A radiation filter can be arranged between the radiation receivers.

Another non-dispersive infrared gas analyser comprising a plurality of detectors arranged one behind the other in series is known from DE 25 05 006 C3.

Furthermore, JP 2003 065 954 A discloses a radiation detector for a non-dispersive infrared gas analyser in which the housing comprises two chambers.

A disadvantage of the disclosed infrared gas analysers is that the detectors are provided by means of a production method in which only a limited number of variations or adaptations of the detectors to a particular gaseous component to be analysed is possible. The essential elements of the detectors, such as the detector chamber or sensor, are fixedly integrated in the detector and cannot be adapted to different gases to be measured. A flexible modification of the detectors or a combination of differently designed detectors is not possible.

The problem addressed by the invention is that of providing a radiation detector which does not have the disadvantages of the known radiation detectors and which is simple to produce.

This problem is solved by a radiation detector having the features according to the invention. Advantageous embodiments of the radiation detector are given below.

According to the invention, the housing of the radiation detector is constructed in a modular manner and comprises a base element comprising the channel, the separating element and the measuring system fastened in the receiving element, and a first and a second outer element which can in each case be connected to the base element and in each case enclose a detector chamber, the outer elements comprising openings located in the beam path of the infrared radiation and the openings being sealed in a gas-tight manner by means of a radiolucent window, the receiving element and the first and second outer elements being joined to the base element. The base element and the outer elements can be referred to as modular components within the meaning of the invention. The measuring gas, according to the invention, designates a gas mixture that is to be quantitively analysed using the gas analyser. The modular design of the radiation detector makes it possible to adapt the detector to the desired intended use, or rather to the measuring gas component to be determined in each case, in a simple and above all cost-effective manner. A base element comprising the measuring system required for the measurement is provided which, according to the relevant intended use, can be complemented by corresponding outer elements which are selected depending on the measuring gas component to be analysed.

By means of the modular construction, it is possible to design the detector chambers such that they are geometrically different from one another, without the base element having to be structurally altered. In a preferred embodiment of the invention, the outer elements can be designed to have different lengths, such that the detector chambers have different lengths in the axial direction. It is known that differing absorption of the measuring gas components can be achieved either by means of different absorption coefficients or by means of different concentrations. According to the Lambert-Beer law, the absorption is also dependent on the chamber length. The lower the absorption coefficient, concentration and chamber length of a product, the greater the linearity of an absorption curve with respect to changing concentrations. A different curvature of the absorption curve for different absorption values leads to a measurement curve, after the measuring instruments have usually been calibrated, and an actual measurement curve not always corresponding. However, it has been shown that this shift can be compensated for by appropriately selecting the chamber length. The invention according to the preferred embodiment makes it possible to alter the chamber lengths in a simple manner by correspondingly adapting the outer elements to the measuring gases or measuring gas components to be analysed.

Not only does the length of the detector chamber affect the measurement quality of the radiation detector, so too does the ratio of the detector chamber lengths to one another. The ratio can be altered on the one hand by means of different chamber lengths and on the other hand by altering the installation position of the separating element in the base element. The lengths of the detector chambers in the axial direction can also be varied by altering the installation position of the separating element, such that a chamber is smaller or bigger in relation to the other chamber and the ratio of chamber lengths is not 1:1.

The modular construction also simplifies the arrangement of a plurality of radiation detectors on an optical bench. A plurality of radiation detectors can be arranged in a coaxial manner one behind the other on the optical bench in the beam path of the infrared radiation, in order for example to determine different measuring gas components in the measuring gas, the chamber length of individual detectors being adaptable to the measuring gas component to be determined in each case. In this way, the measurement quality can be significantly improved.

In order to achieve a stable connection between the receiving element and the measuring system, in one embodiment of the invention, the receiving element is made of a weldable material, the measuring system being welded into the receiving element. By exchanging the receiving element with the welded-in measuring system, the radiation detector can later be repaired in a simple manner. In addition, the functionality of the measuring system can be tested after said measuring system has been fastened to the receiving element and before it has been installed in the base element, which leads to an improvement in yield. Advantageously, the measuring system occupies the entire receiving element and the detector chambers are each pneumatically connected to the measuring system by means of a channel. The receiving element comprising the welded-in measuring system is connected to the base element in particular in a gas-tight manner, there being a pneumatic connection in the form of the channel between the measuring system and the detector chambers, each detector chamber therefore being pneumatically connected to the measuring system. For this purpose, the receiving element can comprise a radial bore which establishes a connection between the channel in the base element and the measuring system. The channel can also be designed as a radial bore in the base element.

The radiation detector can comprise connection regions, such as a flange, which make it possible to install the detector in existing infrared gas analysers at a later time. As a result, the radiation detector can be incorporated in infrared gas analysers by means of small-flange technology. The modular components can also comprise connection regions by means of which the components can be joined together. It is preferred for the receiving element and the first and second outer elements to be joined to the base element by means of gluing, welding or soldering. By virtue of the modular construction of the radiation detector, the joining process can be varied according to the material of the modular components, according to the intended use of the radiation detector or depending on other components integrated in the radiation detector.

The radiation detector, i.e. the modular components, can be produced from a metal or an alloy, such as stainless steel. In another embodiment of the invention, the base element, the first outer element and/or the second outer element are made of aluminium. An advantage of the preferred embodiment is that the modular components do not have to be welded together, which greatly simplifies the production process. Moreover, there is no need for a surface treatment of the detector chambers, it being of possible advantage, depending on the measuring gas in question, to carry out a surface treatment in order to ensure long-term stability of the radiation detector if the radiation detector is being used for the analysis of aggressive gases.

According to the invention, it is proposed for the modular components made of aluminium to be joined together by means of soldering or gluing, i.e. the receiving element and the first and second outer elements are joined to the base element being means of gluing or soldering. In this way, not only can the high temperatures occurring during welding be avoided, but the production of the radiation detector can also be made simpler and more cost-effective.

Furthermore, it is advantageous if an optical filter located in the beam path of the infrared radiation is attached to the separating element or a radiolucent window. An interference filter, an absorption filter or a transmission filter, for example, can be used as the optical filter. Because the temperatures in the case of gluing are lower than in the case of welding, the optical filter can even be attached to the separating element or one of the radiolucent windows built into the outer elements during mounting of the radiation detector. The optical filter can reduce cross-sensitivity, which is potentially caused by gaseous components in the measuring gas.

It is further proposed to use a gas filter in addition or complementarily to the optical filter in order to reduce cross-sensitivity. For this purpose, at least one outer element can comprise a filter chamber that is located in the beam path of the infrared radiation, is separated from the detector chambers in a gas-tight manner and is filled with a filter gas. An advantage of the gas filter is that it can be filled with filter gas in an application-specific manner. The filter gas can optionally be adapted to the relevant use. Light can be absorbed from the infrared radiation by means of the gas filter in a wavelength-specific manner.

According to the invention, it is proposed for the separating element to be designed as a window that is permeable to infrared radiation and impermeable to gas. The separating element can for example be produced from calcium fluoride or barium fluoride and integrated in the base element by means of gluing, welding or soldering. It may be advantageous if the separating element is connected to the base element and the windows are connected to the outer elements in a gas-tight manner by means of an intermediate frame. The intermediate frame may be sealed in a gas-tight manner by means of a glass solder.

In one embodiment, the radiation detector according to the invention may be designed to be impermeable to infrared radiation on account of at least one window being a window provided with a radioreflective layer or a radioreflective pane.

According to the invention, a non-dispersive infrared gas analyser is further provided which comprises a radiation detector described, at least one additional radiation detector being arranged behind the first radiation detector and filled with the same or another measuring gas. A plurality of radiation detectors can be arranged in a coaxial manner one behind the other on an optical bench and, on account of windows in the detectors that are permeable to infrared radiation, it can be ensured that the infrared radiation correspondingly passes through the detectors arranged one behind the other. By virtue of this arrangement, a plurality of measuring gas components can be detected in a measuring gas and by virtue of a corresponding cuvette selection, the concentration can be determined. The detection of strongly and weakly absorbing measuring gas components is also possible by virtue of the preferred non-dispersive infrared gas analyser. Advantageously, a radiation detector acts as a gas filter for the next radiation detector, since infrared radiation is absorbed in a wavelength-specific manner by the measuring gas contained in the detector. In order to further reduce the susceptibility to cross-sensitivity, an optical filter can be arranged between the first and the additional radiation detector.

Figure 2:
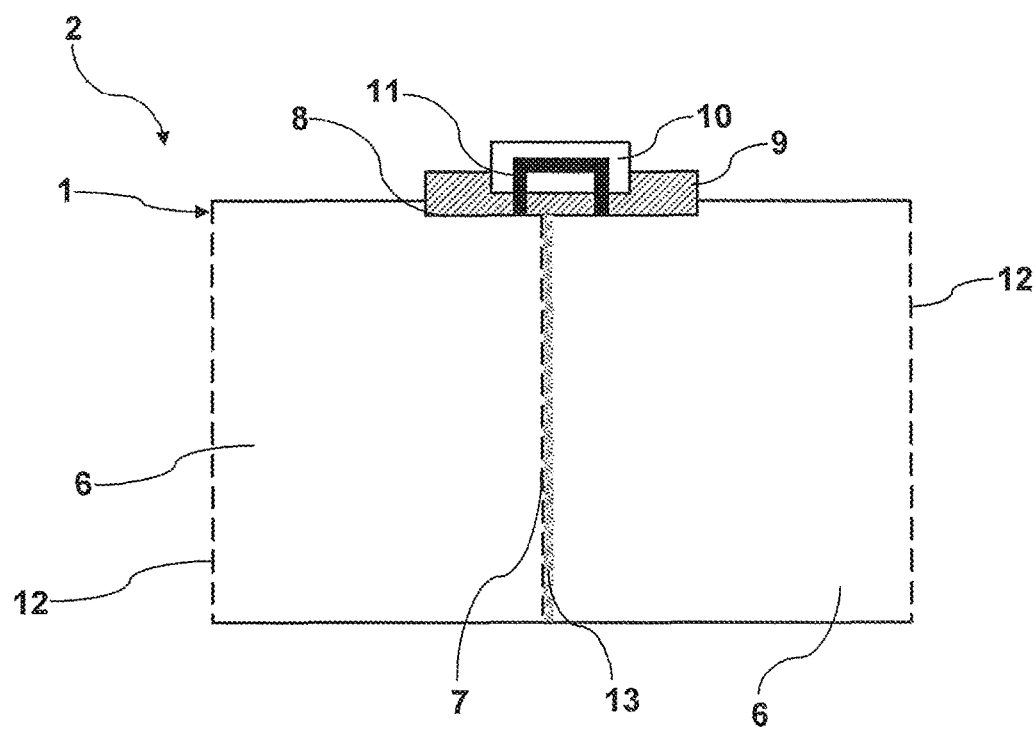
Figure 3:
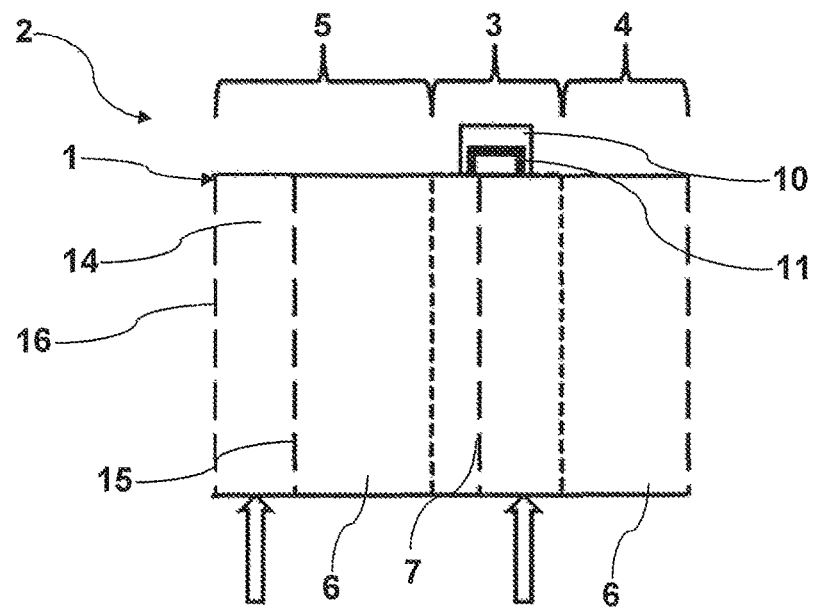
Figure 4:
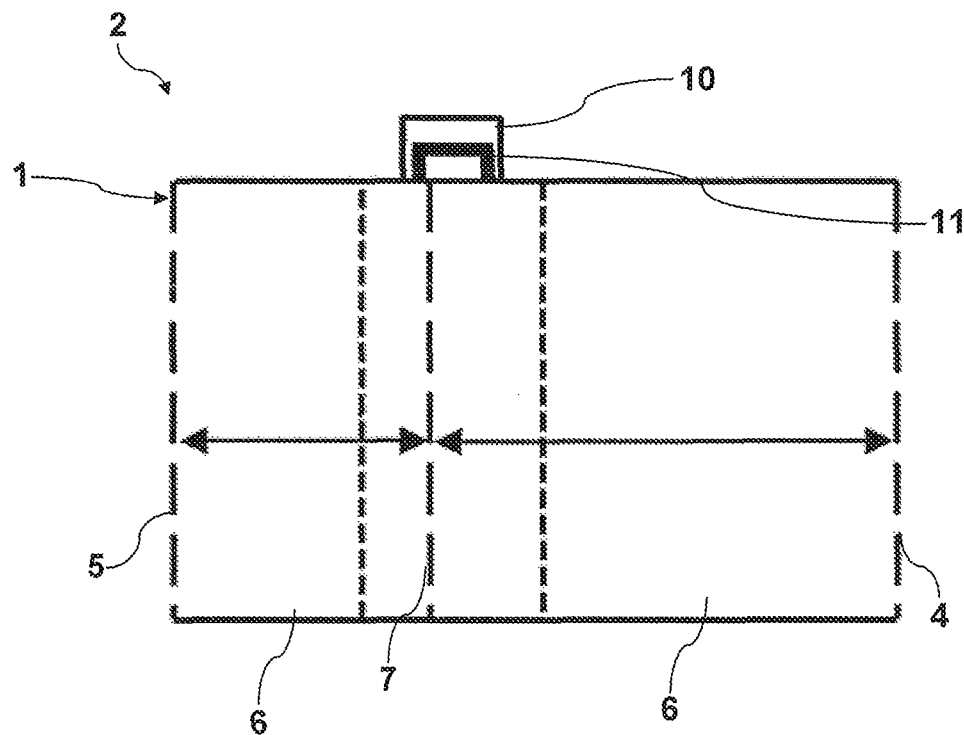
Figure 5:
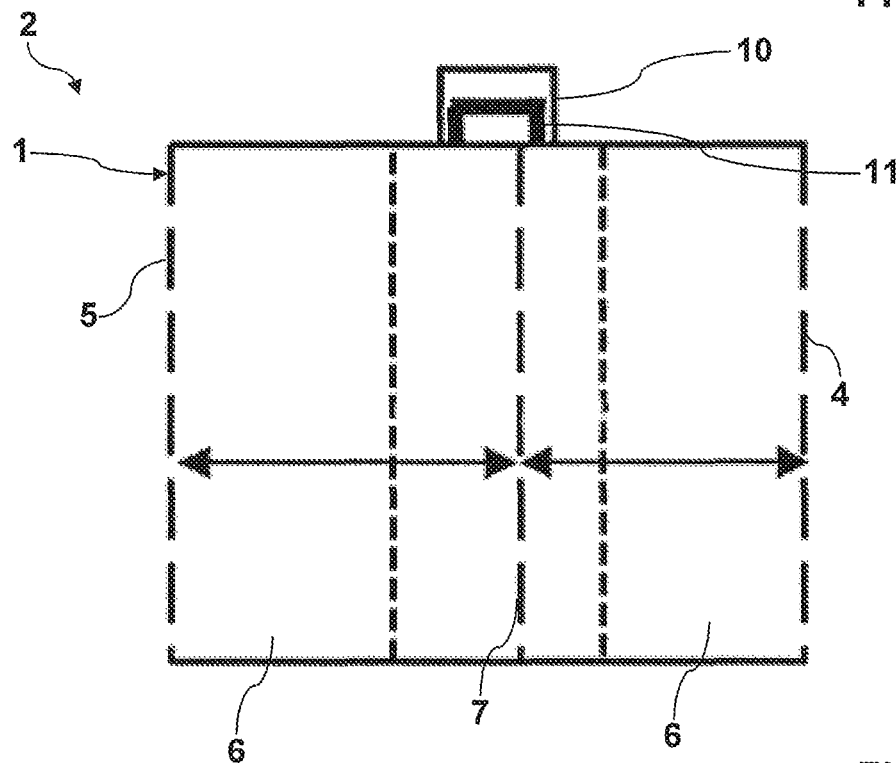
Figure 6:
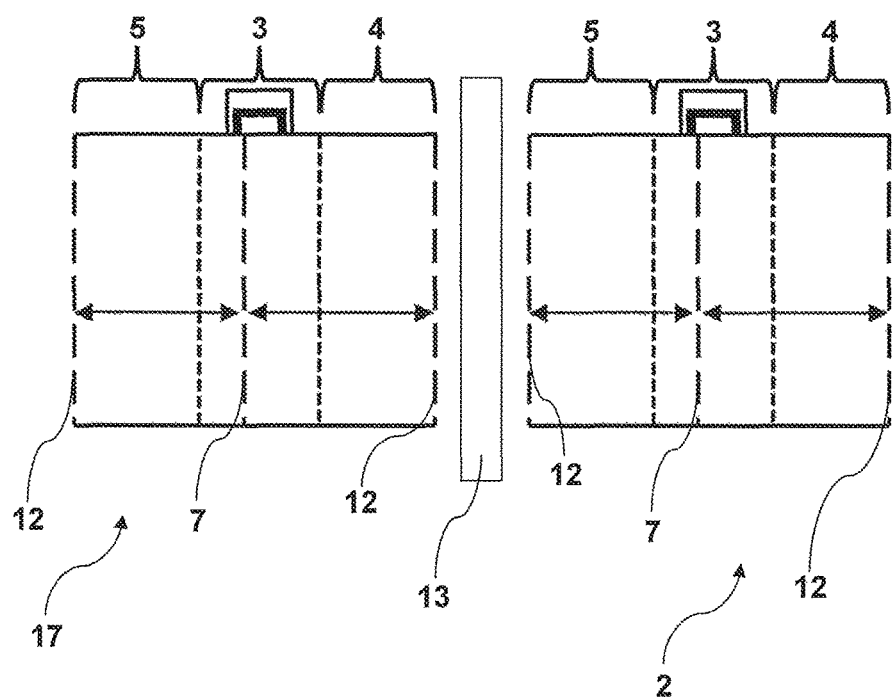

The invention will be described in greater detail in the following with reference to embodiments of the invention shown in the drawings, in which:

FIG. 1 is a cross section through a housing of a radiation detector,

FIG. 2 is a cross section through a housing of a radiation detector comprising an optical filter, FIG. 3 is a cross section through a housing of a radiation detector comprising a gas filter, FIG. 4 is a cross section through a housing of a radiation detector comprising outer elements of different lengths, FIG. 5 is a cross section through a housing of a radiation detector comprising detector chambers of different lengths, and FIG. 6 shows a multiple arrangement of radiation detectors.

The housing 1 of the radiation detector 2 shown in FIG. 1 is constructed in a modular manner and is composed of a base element 3 and a first and a second outer element 4, 5, it being possible to consider the outer elements 4, 5 as a front outer element 4 and a rear outer element 5 on the basis that they are installed in an infrared gas analyser. The base element 3 and the outer elements 4, 5 can be referred to as modular components. The base element 3 and the outer elements 4, 5 form two detector chambers 6 which are separated by means of a separating element 7 that is permeable to infrared radiation and impermeable to gas. The separating element 7 can be designed as a window that is permeable to infrared radiation and impermeable to gas, and can be arranged for example in a recess (not shown) in the base element.

As shown in FIG. 2, the base element 3 comprises a contact surface 8 on the upper face thereof which can for example be formed by a step or a recess. A receiving element 9 for receiving a measuring system 10 comprising a flow-sensitive or pressure-sensitive sensor can be fastened to the contact surface 8. Each detector chamber 9 is pneumatically connected to the receiving element 9, or rather to the measuring system 10, by means of a channel 11 that is open to gas and extends in the housing 1, or more precisely in the base element 3. The channel 11 may be introduced into the base element 3 as a radial bore.

The receiving element 9 is made of a weldable material, such as the alloy Kovar, which consists of iron, nickel and cobalt. The measuring system 10 is welded into the receiving element 9, the measuring system 10 being fastened in the receiving element 9 such that there is a connection, which is open to gas, to the channel 11 and accordingly to the detector chambers 6. The channel 11 extends in as straight a line as possible from the detector chambers 6 to the measuring system 10 in order to thus achieve as large a measuring effect as possible. In order for the measuring effect not to be influenced by different channel geometries, the channels 11 which open into the respective detector chambers 6 and which each pneumatically connect a detector chamber 6 to the measuring system 10 have the same, or at least a similar, geometric shape.

The outer elements 4, 5 are arranged on both sides of and coaxially to the base element 3 and each enclose a detector chamber 6. In other words, the detector chambers 6 are each formed of one outer element 4, 5 and the base element 3. The outer elements 4, 5 comprise openings located in the beam path of the infrared radiation, the openings being sealed in a gas-tight manner by means of a radiolucent window 12. The separating element 7 may also be designed as a window that is permeable to infrared radiation and impermeable to gas.

The windows 12 and the separating element 7 may for example by produced from calcium fluoride. If the windows 12 are not directly introduced into the openings in a gas-tight manner by means of a joining process, the windows 12 and accordingly the separating element 7 designed as a window may be connected to the outer elements 4, 5 or the base element 3 via an annular intermediate frame (not shown in the drawings). The intermediate frame may be produced from an aluminium, gold or silver alloy. The required gas-tight sealing of the windows 12 to the intermediate frame can be achieved by means of thermal sealing by means of a glass solder. The detector chambers 6 can thus receive infrared radiation through the windows 12 and the separating element 7.

The base element 3 and the outer elements 4, 5 comprise connection regions (not shown) which may for example be designed as annular contact surfaces, steps or flanges, and which make it possible to connect the base element 3 to the first and the second outer element 4, 5. The receiving element 9 and the first and second outer element 4, 5 are joined to the base element in a gas-tight manner by means of gluing, welding or soldering. The outer elements 4, 5 may for example be welded to the base element 3 by means of a weld seam on the periphery thereof. The receiving element 9 is attached to the contact surface 8 of the base element 3 on the outside of the housing and may be joined to the base element 3 by means of gluing or soldering. A modular design of the radiation detector 2 is thus possible, which can be adapted to a variety of applications. Moreover, the functionality of the measuring system 10 can be tested after said measuring system has been fastened in the receiving element 9 and before it has been installed in the radiation detector 2. In the event of loss of function, it is also possible to exchange the measuring system 10 in a simple manner.

In order to measure a gaseous component in a measuring gas, the measuring gas can be introduced into the detector chambers 6 by means of a filler nozzle (not shown in the drawings), the detector chambers 6 being separated by means of the radiolucent separating element 7. The infrared radiation is absorbed by the measuring gas in the two detector chambers 6 located one behind the other, the measuring gases heating up differently on account of a differing absorption capacity, and a pressure difference in the detector chambers 6 thus being produced. The pressure difference can be converted into a measuring signal by the measuring system 10, which is coupled into the channel 11 pneumatically interconnecting the two detector chambers 6 and which comprises a flow-sensitive or pressure-sensitive sensor.

As shown in FIG. 2, an optical filter 13 can be arranged in the radiation detector, which optical filter is located on the separating element 7 and in the beam path of the infrared radiation. The optical filter 13 may also be glued to one of the windows 12 arranged in the outer elements 4, 5. Optical filters 13 for reducing cross-sensitivity are only stable up to a certain temperature, and therefore they cannot generally be installed in a radiation detector prior to the completion of same. The radiation detector 2 according to the invention, i.e. the base element 3 and outer elements 4, 5, can be produced from aluminium. The first and second outer elements 4, 5 can then be joined to the base element 3 by means of gluing. Preferred adhesives are cured at a temperature that does not impair the functionality of the pre-installed optical filter.

A ColdBraze method is preferred as the soldering method, in which no fluxing agent is used and in which oxides that may be present in the materials are directly removed, such that a homogenous soldering point is produced.

If the radiation detector 2 is made of aluminium, only the measuring system 10 is introduced into the receiving element 9, which is made of a weldable material, by means of welding. The receiving element 9 having the received measuring system 10 can also be connected to the base element by means of gluing or soldering.

Cross-sensitivity that arises and is caused by a secondary component in the measuring gas can also be minimised by means of a gas filter (shown in FIG. 3). In this case too, the housing 1 of the radiation detector 2 comprises detector chambers 6 which are separated by means of the infrared-permeable separating element 7 and are in each case enclosed by the first and the second outer element 4, 5. At least one outer element 4, 5 comprises a filter chamber 14, which is located in the beam path of the infrared radiation, is separated from the detector chamber 6 in a gas-tight manner, and is filled with an infrared-active filter gas and thus functions as a gas filter. The filter chamber 14 is a chamber that is separated from the detector chamber 6 in a gas-tight manner and is formed for example of an additional infrared-permeable and gas-impermeable separating wall 15 and an outer wall 16 of the outer element 5. The outer wall 16 may be designed as a window 12. The separating wall 15 may be inserted into the outer element 5 by means of gluing, welding or soldering. The filter gas, depending on the intended use of the radiation detector 2, may be filled into the filter chamber 14 and the measuring gas into the detector chambers 6 via a supply point or filler nozzle (shown in FIG. 3 as a direction arrow). The gas filter is advantageous in particular if radiation detectors 2 are in a multiple arrangement and for example placed on an optical bench. The gas filter filters incoming radiation for the radiation detector that follows, such that any cross-sensitivity that arises is minimised.

FIGS. 4 and 5 show a radiation detector 2 comprising a housing 1 and a base element 3, which comprises a measuring system 10 and a channel 11 connecting the detector chambers 6 to the measuring system, at least one detector chamber 6 being lengthened in the axial direction. In FIG. 4, this is achieved by axially lengthening an outer element 4, whereas in FIG. 5 the installation orientation or installation position of the separating element 7 in the base element 3 of the radiation detector 2 is altered. The respective chamber lengths are illustrated by the delimitation arrows in FIGS. 4 and 5. The detector chambers 6 have different lengths and can thus accommodate different volumes of gas. The chamber lengths and also the ratio of the chamber lengths to one another lead to the radiation detector 2 having good linearity and an improved signal-to-noise ratio, as a result of which the quality of the measurement is significantly improved.

For individual arrangement of the radiation detectors 2, at least one window 12 can be a window 12 provided with a radioreflective layer or a radioreflective pane, such that radiative effectiveness is increased. The wall surfaces of the detector chambers can also have a radioreflective surface finish or coating.

As shown in FIG. 6, radiation detectors 2 comprising the base element 3 and the outer elements 4, 5 can be placed in a multiple arrangement one behind the other on account of their modular construction. For multiple arrangement, at least one additional radiation detector 17 is arranged coaxially behind the first radiation detector 2, said additional radiation detector being filled with the same or another measuring gas. An optical filter 13 or a gas filter can be arranged between the first and the additional radiation detector 2, 17. By virtue of the multiple arrangement, simultaneous detection of a plurality of gaseous components in a measuring gas sample is possible. The infrared radiation strikes the first radiation detector 2 comprising infrared-permeable windows 12 and the beams passing therethrough strike the additional radiation detector 17, which is arranged coaxially behind the first radiation detector 2. The optical filter 13, for example a transmission filter, is arranged in the beam path between the two radiation detectors 2 and is permeable to wavelength-specific light beams. It is thus possible to determine a plurality of components in a measuring gas using the modular radiation detectors 2, 17. In order to improve the measurements, the chambers may be placed in different locations. In order to determine further components in a measuring gas, a corresponding number of additional radiation detectors 17 may be arranged in the beam path of the first radiation detector 2.

The invention claimed is:

1. Radiation detector for a non-dispersive infrared gas analyzer, comprising two detector chambers which are surrounded by a housing and separated by a separating element that is permeable to infrared radiation and impermeable to gas, which detector chambers can be filled with a radiation-absorbing measuring gas, comprising a receiving element which can be attached to a contact surface on an outer face of the housing, and comprising a measuring system which is fastened in said receiving element and comprises a flow-sensitive or pressure-sensitive sensor, each detector chamber being pneumatically connected to the measuring system by means of a channel that extends in the housing and is open to gas, wherein the housing of the radiation detector is constructed in a modular manner and comprises a base element comprising the channel, the separating element and the measuring system fastened in the receiving element, and a first and a second outer element which can in each case be connected to the base element and in each case enclose a detector chamber, and wherein the outer elements comprise openings located in the beam path of the infrared radiation, and the openings are sealed in a gas-tight manner by means of a radiolucent window, the receiving element and the first and second outer elements being joined to the base element.

2. Radiation detector according to claim 1, wherein the receiving element is made of a weldable material and the measuring system is welded into the receiving element.

3. Radiation detector according to claim 1, wherein the separating element is designed as a window that is permeable to infrared radiation and impermeable to gas.

4. Radiation detector according to claim 1, wherein the separating element is connected to the base element and the windows are connected to the outer elements in a gas-tight manner by means of an intermediate frame.

5. Radiation detector according to claim 1, wherein at least one window is a window provided with a radioreflective layer or a radioreflective pane.

6. Radiation detector according to claim 1, wherein the outer elements are designed to have different lengths, such that the detector chambers have different lengths in the axial direction.

7. Radiation detector according to claim 1, wherein at least one outer element comprises a filter chamber that is located in the beam path of the infrared radiation, is separated from the detector chambers in a gas-tight manner and is filled with a filter gas.

8. Radiation detector according to claim 1, wherein the receiving element and the first and second outer elements are joined to the base element by means of gluing, welding or soldering.

9. Radiation detector according to claim 1, wherein the base element and the first and/or the second outer element are made of aluminum.

10. Radiation detector according to claim 9, wherein an optical filter located in the beam path of the infrared radiation is attached to the separating element or a radiolucent window.

11. Non-dispersive infrared gas analyzer comprising a radiation detector according to claim 1, wherein at least one additional radiation detector is arranged behind the first radiation detector and is filled with the same or another measuring gas.

12. Non-dispersive infrared gas analyzer according to claim 11, wherein an optical filter is arranged between the first and the additional radiation detector.

* * * * *